United States Patent
Williamson

(12) 
(10) Patent No.: US 6,265,600 B1
(45) Date of Patent: Jul. 24, 2001

(54) ACTIVATED PROPENES AS COLOR COUPLERS METHOD FOR THE PRODUCTION THEREOF

(75) Inventor: Hugh Martin Williamson, Hanwell (GB)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 08/098,334

(22) PCT Filed: Jan. 16, 1992

(86) PCT No.: PCT/EP92/00079

§ 371 Date: Jul. 30, 1993

§ 102(e) Date: Jul. 30, 1993

(87) PCT Pub. No.: WO92/14189

PCT Pub. Date: Aug. 20, 1992

(30) Foreign Application Priority Data

Jan. 13, 1991 (GB) .................................. 9102094

(51) Int. Cl.⁷ .................................. C07C 255/00
(52) U.S. Cl. ............................. 558/303; 558/403
(58) Field of Search ...................... 558/303, 403

(56) References Cited

U.S. PATENT DOCUMENTS 4,871,652 10/1989 Normandin .......................... 430/387

FOREIGN PATENT DOCUMENTS 358186 9/1989 (EP) .
431374 6/1991 (EP) .

*Primary Examiner*—Paul J. Killos
(74) *Attorney, Agent, or Firm*—Arthure E. Kluegel

(57) ABSTRACT

The invention provides novel photographic compositions comprising a propene isomer of the formula

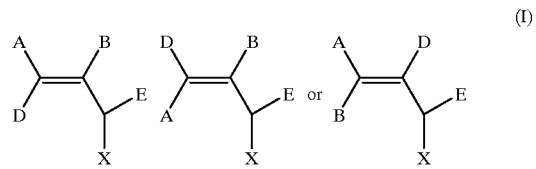

(I)

wherein A B or E, each individually represent hydrogen, or an electron withdrawing group, selected for example from —CN, —NO₂, —SO₂R, —SO₂NH—, —CO₂R, —COR, —CONHR, —CONHAr, —CF₃ halogen, amino, aryl, aralkyl, alkyl, cycloalkyl, alkyl (carbonyl)oxy, aryl (carbonyl)oxy, carboxy, alkoxycarbonyl, aryloxycarbonyl, carbamomyl, acyl, alkylaminocarbonyl, arylaminocarbonyl, alkoxycarbonylamino, acylamino, ureido, alkylsulphonylamino, arylsulphonylamino, sulphamoylamino, alkylsulphonyl, arylsulphonyl, sulphamoyl, imido, alkylthio, arylthio and heterocycles; the invention also provides a propene isomer of the formula I wherein D represents a group of the formula Ar—L— wherein Ar is a phenyl group optionally substituted with one or more substituents, and —L— is a linking group incorporating a lone pair of electrons; and A, B, E and X are defined as R is above defined. The activated propenes of the above formulae are novel colour couplers which react with oxidised developer under alkaline conditions to give magenta dyes.

10 Claims, No Drawings

ACTIVATED PROPENES AS COLOR COUPLERS METHOD FOR THE PRODUCTION THEREOF

This application is a 371 of PCT/EP92/00079.

DESCRIPTION

The present invention relates to the production of activated propenes as colour couplers. The invention particularly relates to the production of magenta colour couplers for use in silver halide imaging systems where dyes are formed by oxidative coupling within a photographic layer. Previously pyrazolone couplers such as that described in U.S. Pat. No. 260,788 have been used. However such pyrazolones are so reactive that the efficiency of dye formation is reduced due to side reactions during photographic processing. Further they require difficult methods of synthesis and have the additional problem of a substantial secondary adsorption peak in the visible spectrum which has an adverse effect on colour reproduction.

This problem has been addressed in U.S. Pat. No. 4,871, 652 by the production of complex cynano-substituted couplers which overcome some of these disadvantages.

Cyan couplers, have been disclosed in EP-A-0,431,374 which is an intervening publication, said couplers being selected from certain activated propenes.

According to the invention there is provided a method for the production of an activated propene of the formula (I)

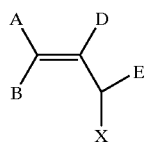

(I)

wherein D represents a group of the formula Ar—L— wherein Ar is a phenyl group, optionally substituted with one or more substituents, and —L— is a linking group incorporating a lone pair of electrons, and wherein the substituents A, B and E each individually represent hydrogen or an electron withdrawing group, and X is hydrogen or a group releasable during a coupling reaction, with the proviso that at least one of A, B and E is a nitrile group; which comprises subjecting a substituted imidate of the formula (III)

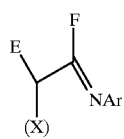

(III)

wherein F is a $C_1$ to $C_6$ alkoxy group, to a condensation reaction in the presence of a base and an activated methylene compound.

The electron withdrawing group may be selected from selected from hydrogen, —CN, —NO$_2$, —SO$_2$R, —SO$_2$NH—, —CO$_2$R, —COR, —CONHR, —CONHAr, —CF$_3$ halogen, amino aryl, aralkyl, alkyl, cycloalkyl, alkyl (carbonyl)oxy, aryl (carbonyl)oxy, carboxy, alkoxycarbonyl, aryloxycarbonyl, carbamomyl, acyl, alkylaminocarbonyl, arylaminocarbonyl, alkoxycarbonylamino, acylamino, ureido, alkylsulphonylamino, arylsulphonylamino, sulphamoylamino, alkylsulphonyl, arylsulphonyl, sulphamoyl, imido, alkylthio, arylthio or a heterocycle;

Examples of the substituent D incorporating the lone pair of electrons are —NH$_2$, —NHR, —NR$^1$R$^2$-, —OR, —OAr, —SAr, —SR— alkyl(carbonyl)oxy, aryl(carbonyl)oxy, carbamoyl, alkoxycarbonylamino, acylamino, ureido, alkylsulphonylamino, or an arylsulphonylamino group.

Examples of substituents on Ar are:- halogens, —CN, —NO$_2$, —SR, —SO$_2$R, —SO$_2$NHR, —OR, —OCOR, —CO$_2$R, —COR, —CONHR, —CO$_2$H, —NHR, —NR$^1$R$^2$, —NHSO$_2$R, —NHCO$_2$R, —NHCONHR, —CF$_3$, aryl, aralkyl, alkyl and cycloalkyl.
with one or more substituents and —L— is a linking group incorporating a lone pair of electrons.

Examples of substituents on Ar are:- halogens, —CN, —NO$_2$—SR, —SO$_2$R, —SO$_2$NHR, —OR, —OCOR, —CO$_2$R, —COR, —CONHR, —CO$_2$H, —NHR, —NR$^1$R$^2$, —NHSO$_2$R, —NHCO$_2$R, —NHCONHR, —CF$_3$, aryl, aralkyl, alkyl and cycloalkyl.

Examples of —L— are:- —NH—, —NR—, —N(COR)—, —NHCONH—, —S—, —SO—, —SO$_2$-, —SO$_2$O—, —O— and -(CO)O—.

The groups hereinbefore designated R, R1 and R2 are each defined as alkyl or aryl, any of which may be substituted.

The substituent X may be H or any coupling off group, for example halogen, —OR, —OAr, —SR, —SAr, wherein the substituent R in the group SR is a primary, secondary or tertiary alkyl group, or a heterocyclic group.

X may also represent or comprise a developement inhibitor, a bleach accelerator, an aryloxy or thioaryl switch group.

Examples of heterocyclic groups capable of being released from compounds of the general formula (I) above by coupling thereof with an oxidised colour developer include pyrroles, pyrazoles, imidazoles, benzimidazoles, benzothiazoles, triazoles, benzotriazoles and tetrazoles.

A preferred form of condensation reaction for the production of a sample compound (IV)

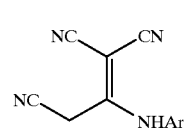

(IV)

may be represented thus:

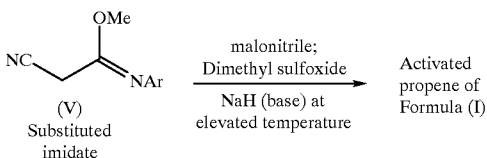

The malonitrile may be substituted by any electron withdrawing grouping equivalent grouping to the CN group, for example an ester group. Such substituted malonitriles may for may for example be ethylcyanoacetate

or diethylmalonate

The OMe group of the substituted imidate may be replaced by a lower alkoxy group of 1 to 6, and preferably 1 to 4, carbon atoms if desired.

The activated propenes produced by this method may be ballasted for example by linking the ballast chain to the Ar group. Suitable ballast agents are:

SAMPLE COMPOUND OF THE INVENTION

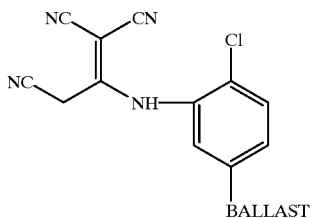

BALLAST GROUPS

1. —$OSO_2C_{16}H_{33}$-n
2. —$OSO_2C_{12}H_{25}$-n
3. —$NHCOC_{11}H_{23}$-n
4. —$CO_2C_{12}H_{25}$-n

5.

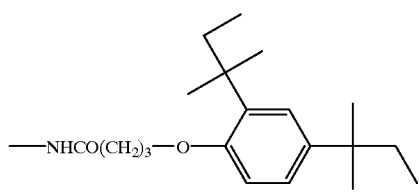

6.

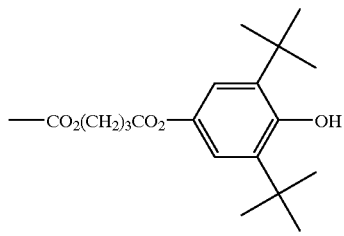

The substituted imidates forming the starting point of this method may be produced for example from malonitrile or a chemically similar compound as follows:

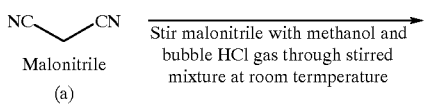

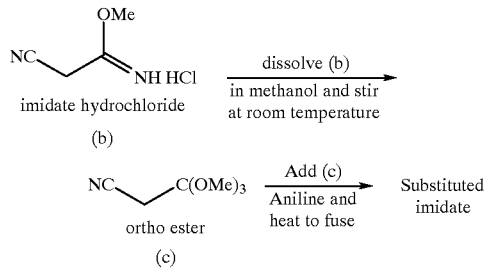

Other methods of this type are described in detail in the examples which follow subsequently.

The activated propenes made according to the invention may be utilized in photographic materials, to which end they may be utilized with sundry known photographic adjuncts.

Development inhibitors are chemical species which are released in an imagewise manner during coupling of the compounds of formula (I) with oxidised colour developer under standard processing conditions utilized in colour photography. After release, such species interact with the silver halide grain to slow down the development process. This has the effect of increasing the perceived sharpness of the image. Development inhibitors are, for example, sulphur-containing compounds, such as mercaptotetrazoles or mercaptobenzothiazoles, or heterocyclic compounds, such as benzotriazoles or benzothiazoles.

Bleach acclerators are chemical species which are released in an imagewise manner during the coupling of compounds of formula (I) with the oxidised colour developer in standard conditions. Upon release, such species act to accelerate the rate at which developed silver is bleached from the emulsion layer. This improves the efficiency of the bleaching stage of the development process and so improves the image quality. It also has the potential to reduce the overall processing time. Bleach accelerators, are, for example, sulphur-containing compounds such as soluble alkyl thiols (e.g. mercaptopropionic acid and dimethylaminoethanethiol) or soluble heterocyclic thiols.

The aryloxy and thioaryl switch groups act to link a colour development inhibitor fragment to a coupler such as a compound of formula (I). Such switches are capable of undergoing an intramolecular rearrangement so as to release the inhibitor fragment. The purpose of the switch group is to delay the release of the inhibitor so the combined switch-inhibitor moiety can diffuse away from the site of initial coupling. By these means, a development inhibitor may be released in a photographic layer adjacent to the site of initial coupling. The release of a development inhibitor in this way results in an improved quality and sharpness.

The above activated propenes react with oxidised colour developing agents under alkaline conditions, for example, between pH 10 and 12 to give magenta dyes. The dyes from this process have no significant absorption in the blue region of the visible spectrum and exhibit good coupling activity as compared with conventional couplers.

The couplers made in accordance with the present invention can be incorporated in a photographic element in known manner, for example by incorporation in droplets of coupler solvents.

The photographic element can be a single colour element or a multicolour element. In a multicolour element, the magenta dye-forming coupler combinations of this invention would usually be associated with a green-sensitive emulsion, although they could be associated with an emulsion sensitised to a different region of the spectrum, or with a panchromatically sensitised, orthochromatically sensitised or unsensitised emulsion. Multicolour elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolour photographic element comprises a support bearing yellow, magenta and cyan dye image-forming units comprising at least one blue-, green- or red-sensitive silver halide emulsion layer having associated therewith at least one yellow, magenta or cyan dye-forming coupler respectively. According to the present invention at least one of these magenta dye-forming couplers may be in combination with a substituted phenol. The element can contain additional layers, such as filter and barrier layers.

In the following discussion of suitable materials for use in emulsions and elements formed with the propenes made according to the invention, reference will be made to Research Disclosure, December 1989, Item 308119, published by Industrial Opportunities Ltd., The Old Harbourmaster's, 8 North Street, Emsworth, Hants PO1O 7DD, U.K. This publication will be identified hereafter as "Research Disclosure".

The silver halide emulsion employed in such elements can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the propene coupler combinations the elements made in accordance with the invention can include additional couplers as described in Research Disclosure Section VII, paragraphs D, E, F and G and the publications cited therein. The coupler combinations for use with the invention and any additional couplers can be incorporated in the elements and emulsions as described in Research Disclosures of Section VII, paragraph C and the publications cited therein.

The photographic elements made with this invention or individual layers thereof, can contain brighteners (see Research Disclosure Section V), antifoggants and stabilisers (see Research Disclosure Section VI), antistain agents and image dye stabiliser (see Research Disclosure Section VII, paragraphs I and J), light absorbing and scattering materials (see Research Disclosure Section VIII), hardners (see Research Disclosure Section X), plasticisers and lubricants (see Research Disclosure Section XII), antistatic agents (see Research Disclosure Section XIII), mating agents (see Research Disclosure Section XVI), and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a colour developing agent to reduce developable silver halide and oxidise the colour developing agent. Oxidised colour developing agent in turn reacts with the coupler to yield a dye.

Preferred colour developing agents are p-phenylene diamines. Especially preferred are 4-amino-3-methyl-N,N-diethylaniline hydrochloride, 4-amino-3-methyl-N-ethyl-N-β-(methanesulphonamido)-ethylaniline sulphate hydrate, 4-amino-3-methyl-N-ethyl-N-β-hydroethylaniline sulphate, 4-amino-3-β-(methanesulphonamido)ethyl-N,N-diethylaniline hydrochloride and 4-amino-N-ethyl-N-(2-methoxyethyl)-m-toluidine di-p-toluene sulphonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable.

Alternatively, a direct positive emulsion can be employed to obtain a positive image.

Development is followed by the conventional steps of bleaching, fixing, or bleach-fixing, to remove silver and silver halide, washing and drying.

The invention will now be described by way of illustration only with reference to the following specific Examples of the invention.

EXAMPLE 1

The production of 4-Chloro-3-(1.1.3-tricyano-prop-1-en-2-ylamino)phenyl hexadecylsulphonate

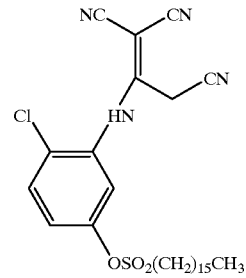

(6)

The compound of formula 6 is prepared by a four-step synthesis as follows:

Methyl Cyanoacetimidate Hydrochloride

A solution of malononitrile (66 g; 1 mole) in diethyl ether (500 ml) and methanol (44 g; 1.38 mole) was cooled to 0° C. by means of an ice-salt bath. The solution was well stirred and hydrogen chloride bubbled through it for 1 h. On standing at 0° C. overnight the product crystallized as a white solid. This was filtered, washed with diethyl ether and allowed to dry to afford the imidate hydrochloride as white crystals (100.6 g; 75% yield). The product was used without characterisation.

Timethyl ortho-cyanoacetate

The methyl imidate ester hydrochloride salt was added to methanol (11) and stirred at room temperature for 18 h. Precipitated ammonium chloride was removed by filtration and the filtrate evaporated to dryness. The residue was partitioned between ether (900 ml) and a saturated sodium carbonate solution (300 ml). The organic layer was separated, dried over magnesium sulphate and filtered. Removal of the ether in vacuo gave the orthoester as a pale yellow oil (75g; 69%). The product was shown to be pure by NMR spectroscopy [2.86δ(2H, s, NC—CH$_2$) and 3.36δ (9H, s, OMe) ] and used without further characterisation.

4-Chloro-3-(2-cyano-1-methoxyethylidineimino) phenyl hexadecylsulphonate

A mixture of the ortho ester (75 g; 0.7 mole), 3-amino-4-chlorophenyl hexadecylsulphonate (21.6 g; 0.5 mole) and a catalytic amount of p-toluenesulphonic acid was heated to 140° C. by means of an oil bath. After 40 minutes, a water pump was used to apply a partial vacuum to the reaction vessel for about 5 minutes. The reaction was then opened to the air and the mixture allowed to cool. The resulting waxy solid was recrystallised from methanol to yield the product imidate as a buff coloured solid (23 g; 89%).

| $C_{26}H_{41}ClN_2O_4S$ | C | H | Cl | N | S |
|---|---|---|---|---|---|
| requires: | 60.9 | 8.1 | 6.9 | 5.5 | 6.3 |
| found: | 61.0 | 7.3 | 6.9 | 5.4 | 6.1 |

4-Chloro-3-(1,1,3-tricyano-prop-1-en-2-ylamino) phenyl hexadecylsulphonate

Sodium hydride (60% dispersion; 0.8 g; 0.02 mole) was added to a solution of malononitrile (1.32 g; 0.02 mole) in dimethyl sulphoxide (DMSO) (100 ml) under a nitrogen atmosphere. The mixture was stirred at room temperature for ca. 40 minutes to leave a pale yellow solution. This was added dropwise to a solution of the imidate (10.25 g; 0.02 mole) in DMSO (50 ml) and the dark coloured mixture was then warmed on a steam-bath at ca. 80° C for 18 h. The solution was poured onto brine (41) to precipitate a brown coloured solid which was extracted into ethyl acetate, dried with magnesium sulphate and filtered. Removal of the solvent under vacuo gave a brown oil which was triturated with 60–80 petroleum to give the product as a buff coloured powder (5.52 g; 50%). The product exhibited satisfactory mass and NMR spectra.

| $CH_{28}H_{39}ClN_4O_3S$ | C | H | Cl | N | S |
|---|---|---|---|---|---|
| requires: | 61.5 | 7.2 | 6.5 | 10.2 | 5.9 |
| found: | 60.9 | 7.1 | 6.6 | 9.7 | 5.8 |

EXAMPLE 2

The production of Diethyl [1-(2-chloro-5-hexadecylsulphonyloxyanilino)-2-cyanoethylidene] malonate (7)

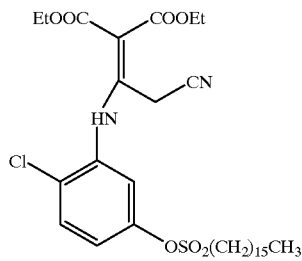

Sodium hydride (60% dispersion; 0.4 g; 0.01 mole) was added to a solution of diethyl malonate (1.6 g; 0.01 mole) in DMSO (50 ml) under a nitrogen atmosphere. The mixture was stirred at room temperature for 40 minutes to leave a colourless solution. This was added dropwise to a solution of the imidate (5.13 g; 0.1 mole) in DMSO (50 ml) and the resulting dark coloured solution was stirred at room temperature for 18 h. The solution was then poured onto dilute hydrochloric acid (1.51) to precipitate a gummy brown solid. This was extracted into ethyl acetate, dried with magnesium sulphate and filtered. Removal of the solvents under vacuo gave a brown oil (6.58 g). On cooling, the product crystallised from this oil as a yellow solid (0.25 g; 4%). The product gave satisfactory NMR and mass spectra.

EXAMPLE 3

A coupler of formula (6) was incorporated into a photographic, green sensitive silver bromoiodide emulsion and coated in the following format:

| Gel supercoat | gelatin | 1.5 gm$^{-2}$ |
|---|---|---|
| Emulsion layer | Silver bromoiodide | 1.61 gm$^{-2}$ |
| | Coupler | 1.04 mmolm$^{-2}$ |
| | Gelatin | 2.42 gm$^{-2}$ |
| | Bis(vinylsulphonyl)-methane (hardener) | 0.06 gm$^{-2}$ |
| Support | Cellulose acetate | |

The coupler dispersion used contained 6% w/w gelatin, 8.8% coupler and coupler solvents in the ratio: coupler: tricresyl phosphate: 2-(2-butoxyethoxy)ethyl acetate 1:0.5:1.5.

The experimental photographic coatings prepared in this way are slit and chopped into 35 mm test strips. These are exposed through a 0–4.0 neutral density step wedge (0.2 ND step increments) and Daylight V, Wratten 9 filters then processed through the following standard C-41 process.

| Developer | 2.5 minutes |
|---|---|
| Bleach | 4 minutes |
| Wash | 2 minutes |
| Fix | 4 minutes |
| Wash | 2 minutes |

For each test strip, step-wedge densities are measured using a Macbeth TD/504/Hewlett Packard 85 automatic transmission densitometer. Measurements of minimum density (Dmin), maximum density (Dmax) and contrast (gamma) are calculated from D log E curves.

A comparison of the photographic results obtained from these tests is shown in Table 1.

TABLE 1

Photographic Performance of Compound 6 vs Control Couplers I, II and III

| Compound | D-min | D-max | Gamma | L-max |
|---|---|---|---|---|
| 6 | 0.29 | 2.24 | 3.06 | 553.5 nm |
| I | 0.13 | 2.32 | 2.29 | 555.5 nm |
| II | 0.15 | 2.77 | 4.01 | 546.5 nm |
| III | 0.14 | 2.62 | 2.08 | 553 nm |

The results show that compound 6 produces a dye of similarly desirable spatial absorption as compound III but has a much higher gamma (context). The dye produced for compound 6 has much lower blue absorption than those for compounds I and II.

COMPOUND I

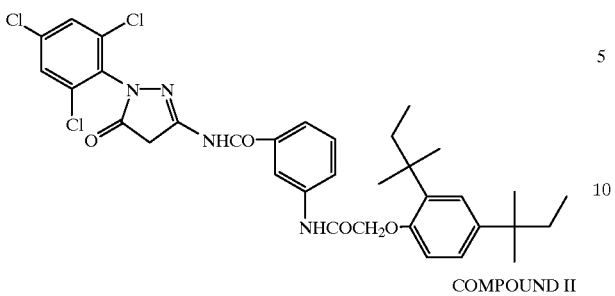

COMPOUND II

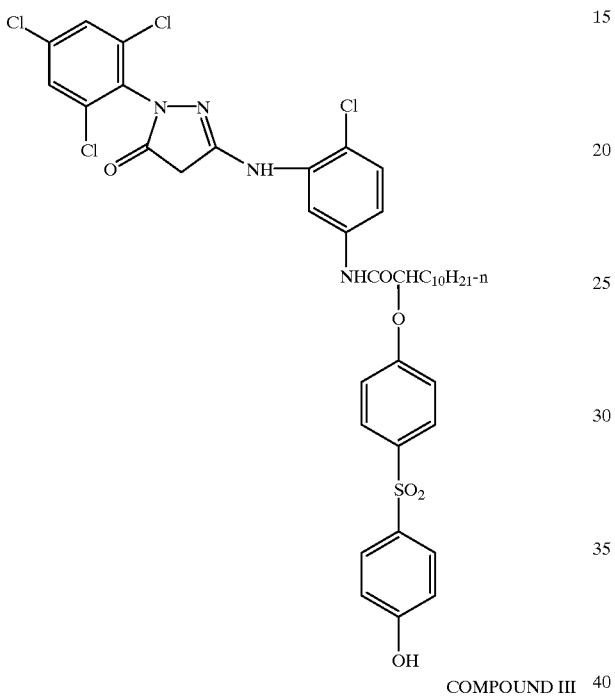

COMPOUND III

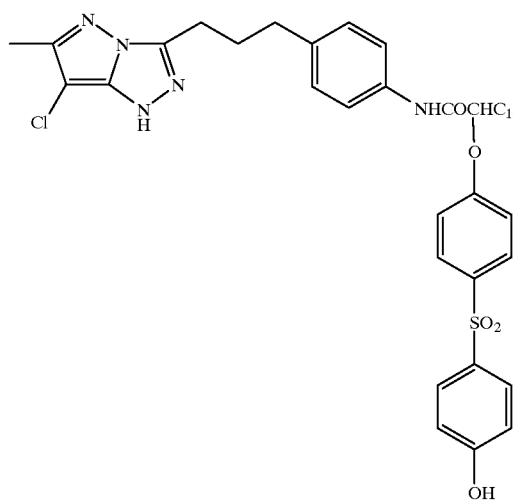

Similarly the compound 7 may be incorporated in photographic elements and produced similar results.

The invention provides therefore novel substituted propenes of the formula given above, photographic compositions comprising propenes of the formula (I), a method for the production of a novel substituted propenes, photographic elements comprising any of the foregoing and an image forming process for incorporation of the same.

What is claimed is:

1. A method for the production of an activated propene of the formula (I)

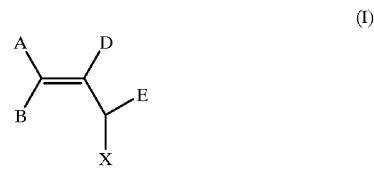

(I)

wherein D represents a group of the formula Ar—L— wherein Ar is a phenyl group, optionally substituted with one or more substituents, and —L— is a linking group incorporating a lone pair of electrons, and wherein the substituents A, B and E each individually represent hydrogen or an electron withdrawing group, and X is hydrogen or a group releasable during a coupling reaction, with the proviso that at least one of A, B and E is a nitrile group; which comprises subjecting a substituted imidate of the formula (III)

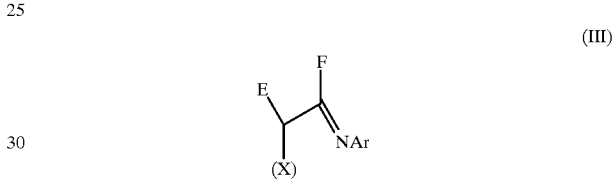

(III)

wherein F is a $C_1$ to $C_6$ alkoxy group and Ar is a substituted or unsubstituted aryl group, to a condensation reaction conducted under a nitrogen atmosphere in the presence of a base and an activated methylene compound.

2. A method according to claim 1 wherein there are two withdrawing groups with one being nitrile and the other being selected from the group consisting of
—CN, —$NO_2$, —$SO_2R$, —$SO_2NH$—, —$CO_2R$, —COR, —CONHR, —CONHAr, —$CF_3$, halogen, alkyl (carbonyl)oxy, aryl (carbonyl)oxy, carboxy, alkoxycarbonyl, aryloxycarbonyl, carbamomyl, acyl, alkylaminocarbonyl, arylaminocarbonyl, acylamino, ureido, alkylsulphonylamino, arylsulphonylamino, sulphamoylamino, alkylsulphonyl, arylsulphonyl, sulphamoyl, imido and a heterocycle wherein R is an alkyl group, substituted or not.

3. A method according to claim 1 wherein X is selected from H, halogen, —OR, —OAr, —SR, and —SAr, and wherein the substituent R in the group SR is a primary, secondary or tertiary alkyl group.

4. A method according to claim 1 wherein D is selected from —$NH_2$, —NHR, —$NR^1R^2$, —OR, —OAr, —SR, —SAr, alkyl (carbonyl)oxy, aryl (carbonyl)oxy, carbamoyl, alkoxycarbonylamino, acylamino, ureido, alkylsulphonylamino, or an arylsulphonylamino group wherein R is a substituted or unsubstituted alkyl group.

5. A method according to claim 4 wherein D is —NHR.

6. A method according to claim 1 wherein a ballast group is linked to said Ar— group.

7. A method according to claim 1 wherein the substituents of the activated methylene compound are selected from the group consisting of
—CN, —$NO_2$, —$SO_2R$, —$SO_2NH$—, —$CO_2R$, —COR, —CONHR, —CONHAr, —$CF_3$, halogen, amino, aryl, aralkyl, alkyl, cycloalkyl, alkyl (carbonyl)oxy, aryl (carbonyl)oxy, carboxy, alkoxycarbonyl, aryloxycarbonyl, carbamomyl, acyl, alkylaminocarbonyl, arylaminocarbonyl, alkoxycarbonylamino, acylamino, ureido, alkylsulphonylamino, arylsulphonylamino, sulphamoylamino, alkylsulphonyl, arylsulphonyl, sulphamoyl, imido, alkylkthio, arylthio and a heterocycle wherein R is an alkyl group, substituted or not.

8. A method according to claim 7 wherein the activated methylene compound carries at least one —CN or ester substitution.

9. A method according to claim 8 wherein the activated methylene compound is malonitrile, ethylcyanoacetate or diethylmalonate; the base is an alkali metal hydride, and the reaction is conducted at an elevated temperature in a chemically compatible solvent.

10. A method according to claim 6 wherein the ballast group linked to said Ar group is selected from the group consisting of 1. —$OSO_2C_{16}H_{33}$-n
2. —$OSO_2C_{12}H_{25}$-n
3. —$NHCOC_{11}H_{23}$-n
4. —$CO_2C_{12}H_{25}$-n
5. —NHCO(CH$_2$)$_3$—O— 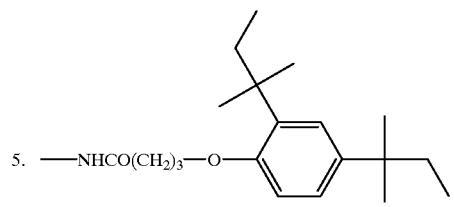
6. —CO$_2$(CH$_2$)$_3$CO$_2$— 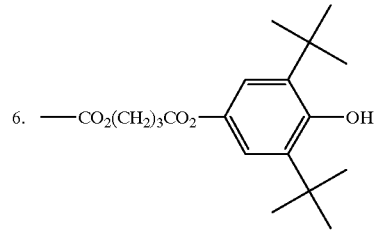

* * * * *